US006849262B2

(12) United States Patent
Ollerenshaw et al.

(10) Patent No.: US 6,849,262 B2
(45) Date of Patent: Feb. 1, 2005

(54) VASCULAR COATING COMPOSITION

(75) Inventors: Jeremy Ollerenshaw, Marietta, GA (US); Umit Yuksel, Kennesaw, GA (US); Kirby S. Black, Acworth, GA (US)

(73) Assignee: Cryolife, Inc., Kennesaw, GA (US)

( * ) Notice: Subject to any disclaimer, the term of this patent is extended or adjusted under 35 U.S.C. 154(b) by 0 days.

(21) Appl. No.: 10/067,331

(22) Filed: Feb. 7, 2002

(65) Prior Publication Data

US 2002/0183244 A1 Dec. 5, 2002

Related U.S. Application Data

(63) Continuation of application No. 09/662,459, filed on Sep. 15, 2000, now Pat. No. 6,372,229.
(60) Provisional application No. 60/153,950, filed on Sep. 15, 1999.

(51) Int. Cl.[7] .............................. A61K 9/00; A61K 2/00; A61K 35/34; A61K 2/06
(52) U.S. Cl. ........................ 424/400; 424/423; 424/569; 623/1.46; 623/1.42; 623/920; 623/921
(58) Field of Search .......................... 514/496; 604/163, 604/95.02; 623/920, 921, 1.46, 1.42; 424/400, 423, 569

(56) References Cited

U.S. PATENT DOCUMENTS

| 4,247,406 A | 1/1981 | Widder et al. |
| 4,979,959 A | 12/1990 | Guire |
| 5,213,580 A | 5/1993 | Slepian et al. |
| 5,385,606 A | 1/1995 | Kowanko |
| 5,800,538 A | 9/1998 | Slepian et al. |
| 5,830,504 A | 11/1998 | Vuori et al. |
| 5,914,345 A | 6/1999 | Slepian et al. |
| 6,372,229 B1 * | 4/2002 | Ollerenshaw et al. ....... 424/400 |

OTHER PUBLICATIONS

Eddy et al, "The Effects of Bioglue® Surgical Adhesive in the Surgical Repair of Aortic Dissection in Sheep", European Association for Cardio–Thoracic Surgery [EACTS], Sep. 1998.

Gundry et al, "Sutureless Coronary Artery Bypass with Biologic Glued Anastomoses: Preliminary In Vivo and In Vitro Results", American Association for Thoracic Surgery, p. 200, Apr. 1999.

Hill–West et al, "Inhibition of thrombosis and intimal thickening by in situ photopolymerization of thin hydrogel barriers", Proc. Natl. Acad. Sci. USA 91:5967–5971 (1994).

* cited by examiner

*Primary Examiner*—Thurman K. Page
*Assistant Examiner*—Blessing Fubara
(74) *Attorney, Agent, or Firm*—Nixon & Vanderhye P.C.

(57) ABSTRACT

This invention relates to methods of coating the lumenal surface of a blood vessel, or other tissue cavity, and to compositions suitable for use in same.

30 Claims, 5 Drawing Sheets

VASCULAR COATING COMPOSITION

This application is a continuation of Ser. No. 09/662,459 filed Sep. 15, 2000, now U.S. Pat. No. 6,372,229 and claims priority from Provisional Application No. 60/153,950, filed Sep. 15, 1999, the entire content of which is incorporated herein by reference.

TECHNICAL FIELD

This invention relates to methods of coating the lumenal surface of a blood vessel, or other tissue cavity, and to compositions suitable for use in same.

BACKGROUND

Various surgical and percutaneous therapies have been developed to reopen blocked channels, conduits, and other lumens, to remove diseased tissue, and to implant substitute tissue, or components thereof. While these therapies are effective, they often simultaneously injure cells or cellular components of the manipulated tissues.

The responses to injuries resulting from therapeutic interventions can cause complications that undo the beneficial effect of the intervention, or create new problems. For example, percutaneous transluminal angioplasty can open obstructed atherosclerotic arteries. However, the balloon-mediated stretch and crush injury to the arterial wall can lead to proliferation of the smooth muscle cells of the media of the artery, resulting in reclosure of the artery ("restenosis") over the following months. This is observed in at least one-third of arteries treated. Another example is in the formation of adhesions after surgery, in which post-operative events result in the formation or proliferation of adventitious tissue that binds internal body surfaces together, causing discomfort, organ malfunction and potential morbidity and mortality. This can occur in many tissues and organs, including the intestine, the peritoneum, the heart, the pericardium, lungs, pleura, etc.

Various interventions have been proposed to minimize such problems. These include the use of stents and coatings in arteries (Slepian, in "Polymeric Endoluminal Paving" Cardiology Clinics 12(14) (November 1994), Slepian, et al, Circulation 88(4):part 2, 1–319 (1993), Hill-West, et al, Proc. Natl. Acad. Sci. USA 91:5967 (1994), U.S. Pat. No. 5,213,580, U.S. Pat. No. 5,800,538). In addition, the use of coatings, gels and fabrics can be used to prevent abdominal and pelvic adhesions (Hill-West et al, Obst. Gyne. 83:59 (1994)). Many of these treatments are administered after the injury has occurred, whether as a result of balloon angioplasty or otherwise, allowing the injured cells to initiate the series of processes involved in clotting, complement activation, and cellular response to release of cytokines, inducers of proliferation, and other biologically active molecules. It is difficult to stop these complex, interrelated processes once they have begun.

The present invention relates to methods, and compositions suitable for use therein, that minimize the reaction of cells and tissues, and of cells nearby or adjacent to them, to a subsequent injury.

SUMMARY OF THE INVENTION

The present invention provides, in one embodiment, a solution to the problem of restenosis following angioplasty. Specifically, the invention provides a method for endoluminal coating that involves application of a material to the interior surface of the involved blood vessel. The present approach is not limited to use in connection with restenosis, however, and can also be effectively employed in any hollow organ to provide local structural support, a smooth surface, improved flow and sealing of lesions. In addition, the coating material can incorporate therapeutic agents such as drugs or cell regeneration factors to accelerate healing processes. Such material with incorporated therapeutic agents can be effectively used to coat surgically or traumatically formed lumens in normally solid organs as well as the native or disease generated lumens of hollow or tubular organs.

Objects and advantages of the present invention will be clear from the description that follows.

DETAILED DESCRIPTION OF THE INVENTION

Figure 1:
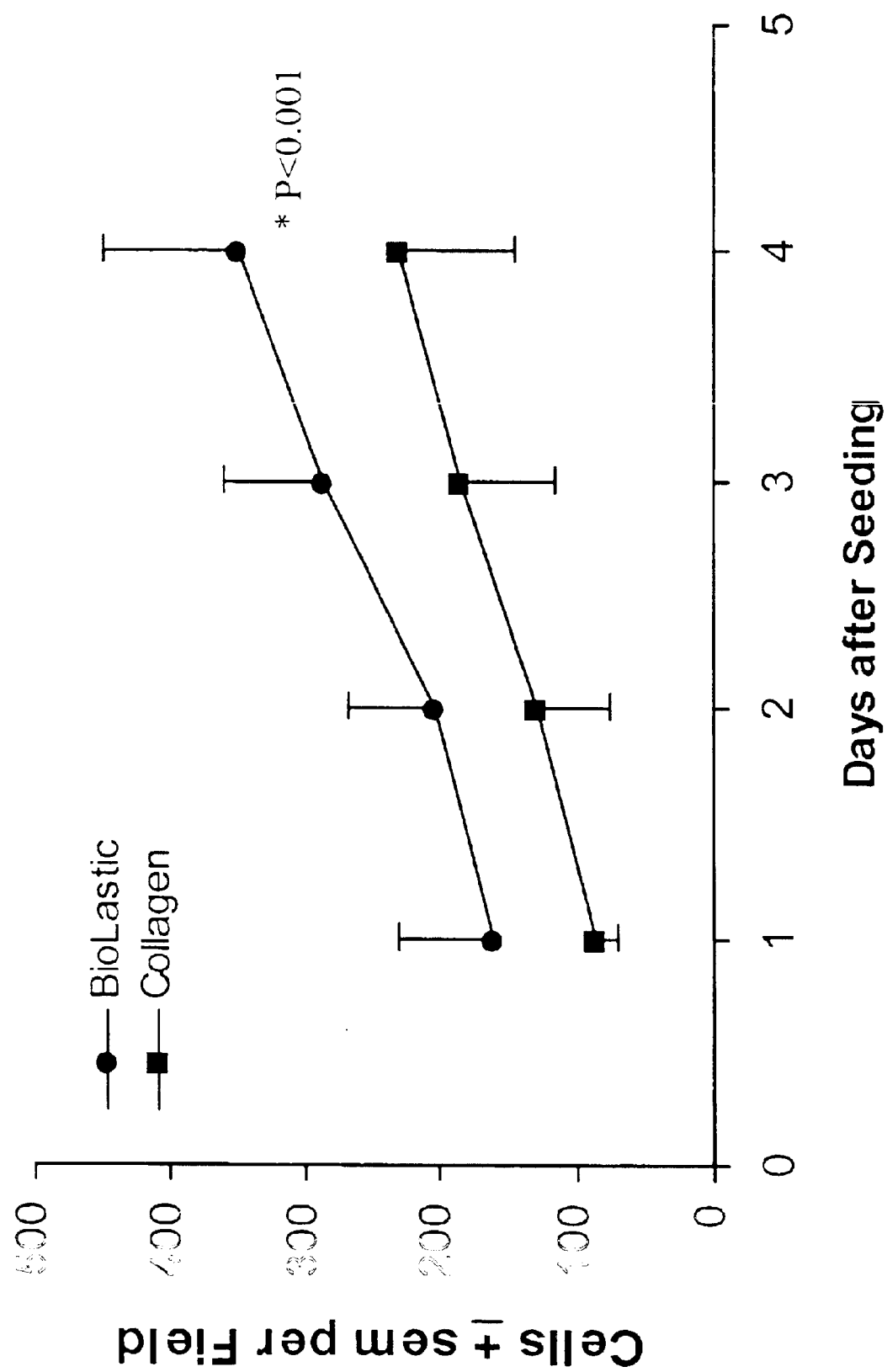
FIG. 1. Graph swing mean±sem for the BIOLASTIC disks versus the collagen-coated control dishes. Cells were counted until confluence and statistical analysis of the effect of the different growth surfaces was made. The cell present on BIOLASTIC disks were in greater number than on collagen coated plates indicating that BIOLASTIC is more suitable than collagen for endothelial cell adherence and growth.

In general, the present invention involves the introduction of a material into a selected location within a lumen in tissue, i.e. an organ, an organ component or cavernous component of an organism, under conditions such that the material forms an adherent coating on the interior surface.

The basic requirements for the material to be used in the present method are biocompatibility and the capacity to adhere to the surface to be coated. Suitable materials for use in the invention are described in U.S. Pat. No. 5,385,606 (Kowanko). Preferred materials comprise hemoglobin or albumin (e.g., bovine albumin) in a 30–55% solution and glutaraldehyde in a 5–15% solution. More preferred materials comprise bovine albumin in a 50% solution and glutaraldehyde in a 5% solution.

Coatings in accordance with the invention can be of varying thicknesses and three-dimensional geometries. The coating can be present of the inner surface of hollow, cavernous, or tubular biological structures (whether natural or artificially formed) in either single or multiple layer configurations. The coating can also be used, where appropriate, to occlude a tissue lumen completely. The material used can be combined with a variety of therapeutic agents for on-site delivery. Examples for use in coronary artery applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), vasodilating agents, i.e., nitrates, calcium channel blocking drugs, anti-proliferative agents, i.e., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in the coatings of the invention. In applications where multiple layers are used, different pharmacological agents can be used in different layers. Moreover, the coating can be used to effect pharmaceutical delivery focally within the vessel wall.

The process of applying the coating of the invention can be carried out using catheters that may incorporate occlusion balloons. The distal end resides at the delivery site and the proximal end remains outside of the patient. Coating materials can be delivered through the lumen or lumens of the catheter. An alternative method of applying the coating is to apply a solution of, for example, glutaraldehyde using, for example, surgical gauze or sponges. The protein solution (e.g., albumin solution) can be applied as a wash onto the treated surface.

In addition to arteries, i.e., coronary, femoral, the aorta, ilial, carotid and vertebro-basilar, the present process can be utilized for other applications such as coating the interior of vascular and dialysis access graft, veins, ureters, urethrae, bronchi, biliary and pancreatic duct systems, the gut, eye, nasal passage, sinus, capsular joint, esophagus, lymphatic system, trachea and spermatic and fallopian tubes. The present method can also be used in other direct clinical applications even at the coronary level. These include but are not limited to the treatment of abrupt vessel reclosure post angioplasty, the "patching" of significant vessel dissection, the sealing of vessel wall "flaps", i.e., secondary to catheter injury or spontaneously occurring, the coating of aneurysmal coronary dilations associated with various vascular diseases. Further, the present invention provides intra-operative uses such as sealing of vessel anostomoses during coronary artery bypass grafting and the provision of a bandaged smooth surface post endarterectomy.

The ultimate in vivo deployed geometry of the material of the invention dictates the final function of the coating. The thinner applications allow the material to function as a coating, sealant and/or partitioning barrier, bandage, and drug depot.

Complex internal applications of thicker layers of the material, such as intra-vessel or intra-luminal applications, can actually provide increased structural support and depending on the amount of the material used in the layer may actually serve in a mechanical role to maintain vessel or organ potency.

Certain aspects of the present invention are described in greater detail in the non-limiting Examples that follow. Details relating to BIOLASTIC can be found, for example, in U.S. Pat. No. 5,385,606 (Kowanko). Those details are incorporated herein by reference.

EXAMPLE 1

Methods

Endothelial Cell Isolation

Human arterial endothelial cells were harvested from human femoral arteries obtained during donor tissue procurement within 2 hours of the time of death. The arteries were first cleaned of adherent fat and connective tissue and all tributaries were suture ligated using 6/0 polypropylene monofilament (Ethicon, Somerville, N.J.) to prevent leakage during subsequent cell harvest. The arterial lumen was then gently washed with Dulbecco's phosphate buffered saline (DPBS, Bio-Whittaker, Walkersville, Md.) and filled with 1 mg/ml type-2 collagenase in DPBS solution (216 U/mg, Worthington, Lakewood N.J.) and warmed to 37° C. to loosen endothelial cells from their sub-endothelial matrix. Incubation with the collagease solution for 15 minutes at 37° C. was found to be adequate. The lumen was then flushed with 8–10 ml DPBS at 4° C. The eluate was centrifuged at 180×g for 10 minutes at 4° C. in tubes containing 10 ml of heat inactivated fetal bovine serum (Bio-Whittaker, Walkersville, Md.) at 4° C. The supernatant was discarded and the pellet resuspended in 2 ml endothelial cell growth media (Clonetics, San Diego, Calif.) supplemented with 6 mg bovine brain extract, 5 mg epidermal growth factor, 0.5 mg hydrocortisone, 10 ml fetal bovine serum and 25 mg gentamicin. Harvested endothelial cell numbers and viability were assessed in a 50 ml aliquot of media by trypan blue exclusion. Verification of cell type was made using immunohistochemistry staining. Endothelial cells were frozen in 10% dimethylsulfoxide containing cell growth media and stored in liquid nitrogen until use.

Endothelial Cell Maintenance Culture

Cultures of endothelial cells were maintained until use at low passage by using cryopreserved cell stocks. After thawing, frozen cell stocks were fed three times weekly and passaged at least once a week in fresh endothelial cell growth media.

BIOLASTIC Disk and Collagen Coating Preparation

BIOLASTIC is comprised of crosslinked bovine albumin. To prepare BIOLASTIC disks, a 45% solution of bovine albumin was pipetted, using a pipetter mixing tip, together with a 10% solution glutaraldehyde between two glass plates that were separated by 0.5 mm spacers. The ratio of albumin to glutaraldehyde present in the mixture is 4:1. This ratio initiates rapid cross-linking which is stable within 2 to 3 minutes. The 0.5 mm thick sheets were then cut into 28 mm diameter disks, which were placed into sealed pouches containing water. Pouches were then sterilized using gamma irradiation (30 kGy). The disks were then removed from the sealed pouches at ambient temperature then placed in 5 ml endothelial cell growth medium for 30 minutes. Prior to seeding, each disk was transferred to a 35 mm polystyrene cell culture plate (Becton Bickinson, Lincoln Park, N.J.) containing 5 ml of endothelial cell growth medium.

The control group consisted 35 mm polystyrene cell culture plates where the inside of individual plates were brushed with a solution of collagen (Cohesion Technologies, Palo Alto, Calif.) and allowed to dry. Endothelial cells have specific substrate requirements for adherence and collagen is commonly used as a coating material For endothelial cell culture. A 5 ml volume of endothelial cell growth medium was added prior to seeding with cells.

Cell Seeding and Counting

To initiate growth determinations, endothelial cells at passage 4 were carefully pipetted onto the surface of five BIOLASTIC disks and five collagen coated 35 mm control plates at a seeding density of $1.25 \times 10^5$ cells/cm$^2$. Growth of cells attached to BIOLASTIC disks and the collagen coated control plates were monitored daily by counting cells within 4 randomly selected microscopic fields of a size 1.8 mm$^2$. Counts were facilitated by capturing video images using an inverted microscope fitted with a 4× objective and a Sony DXC-107 digital camera and a UP5000 video printer. Printed field images were manually counted and an average of cell counts per field was calculated. From these data, growth profiles could be followed for endothelial cells seeded onto BIOLASTic disks and the control collagen-treated culture plates. All results were calculated as the mean number of cells and the standard error from the mean. Statistical differences between groups were calculated using the Student's t test.

Endothelial Cell Staining

At various times during the seeding experiments cultures of endothelial cells growing on BIOLASTIC disks and collagen coated plates were stained with a fluorescent lipophilic dye to visualize the cell morphology. Rapid in situ staining of endothelial cells is now available using the fluorescent lipophilic compound, PKH-26-GL. With minimal sample manipulation the endothelial cell coverage is clearly seen under fluorescent light. BIOLASTIC disks were removed from endothelial cell culture medium and labeled with the PKH26-GL dye (Sigma Chemical Company, St. Louis, Mo.) according to Horan et al (Methods Cell. Biol. 3:469–490 (1990)). Collagen coated plates were stained in a similar way. Briefly, the disks or plates were first rinsed with DPBS prior to labeling with 200 ml of 10 $\mu$M PKH26-GL. After a 10 minute incubation, the disks and plates were rinsed in fetal bovine serum and then with DPBS. The microscope used for visualization was fitted with an epi-fluorescent attachment and a Nikon G-series filter set.

Results

Endothelial Cell Staining

Staining of endothelial cell cultures with the lipophilic dye PKH26-GL was rapid. Cells were visualized within 15 minutes of initiating the staining protocol and showed clear cell outlines, cell-cell contact points and cell nuclei (FIG. 2, FIG. 3).

Growth of Cell Cultures

Figure 2A:
FIGS. 2A and 2B. PKH26-GL labeled sub-confluent cultures of endothelial cells 2 days following seeding on the surface of BIOLASTIC disks (FIG. 2A) and collagen-coated plates (FIG. 2B).
Figure 2B:
Figure 3A:
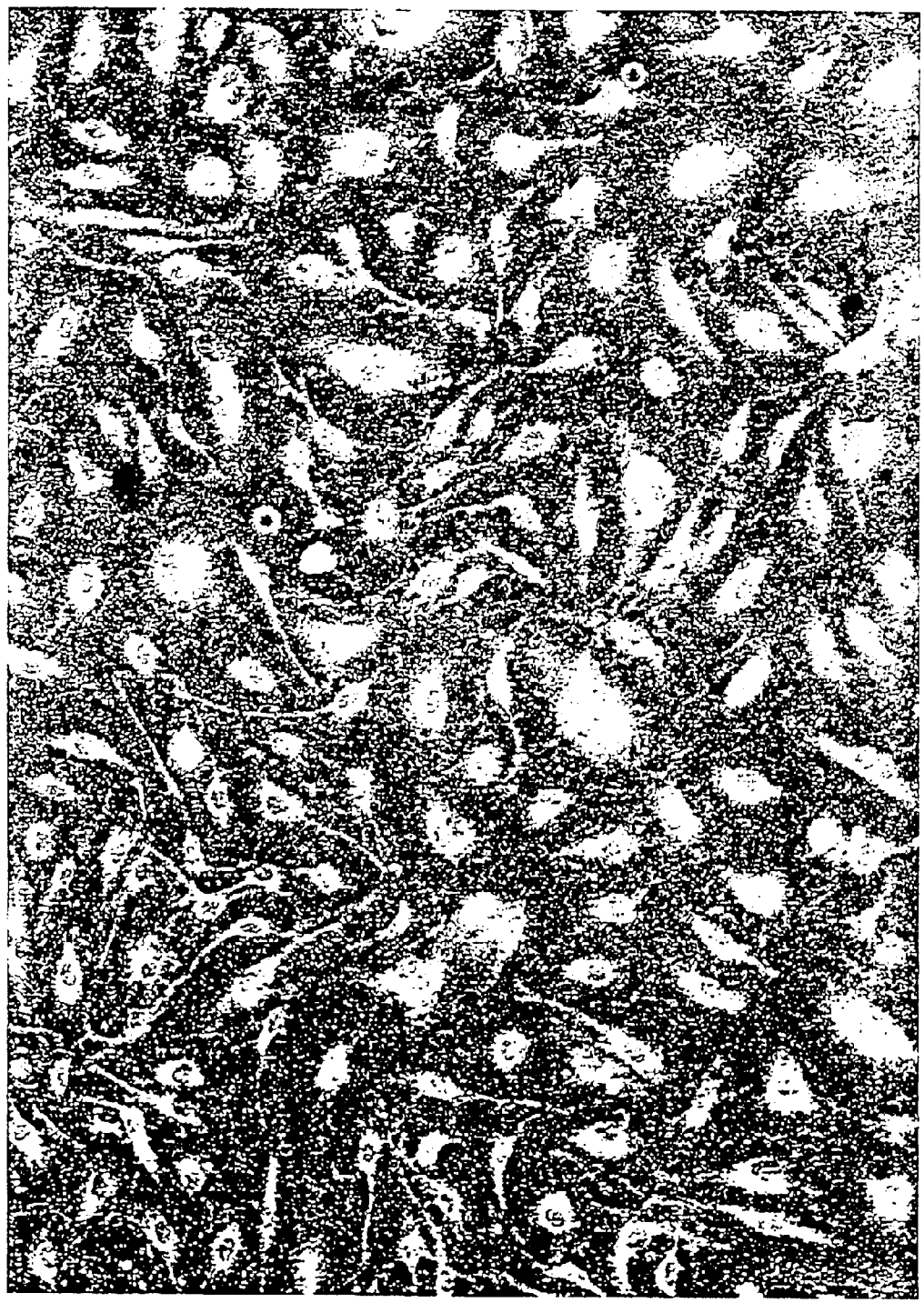
FIGS. 3A and 3B. PKH26-GL labeled confluent cultures of endothelial cells 4 days following seeding on the surface of BIOLASTIC disks (FIG. 3A) and collagen-coated plates (FIG. 3B).
Figure 3B:
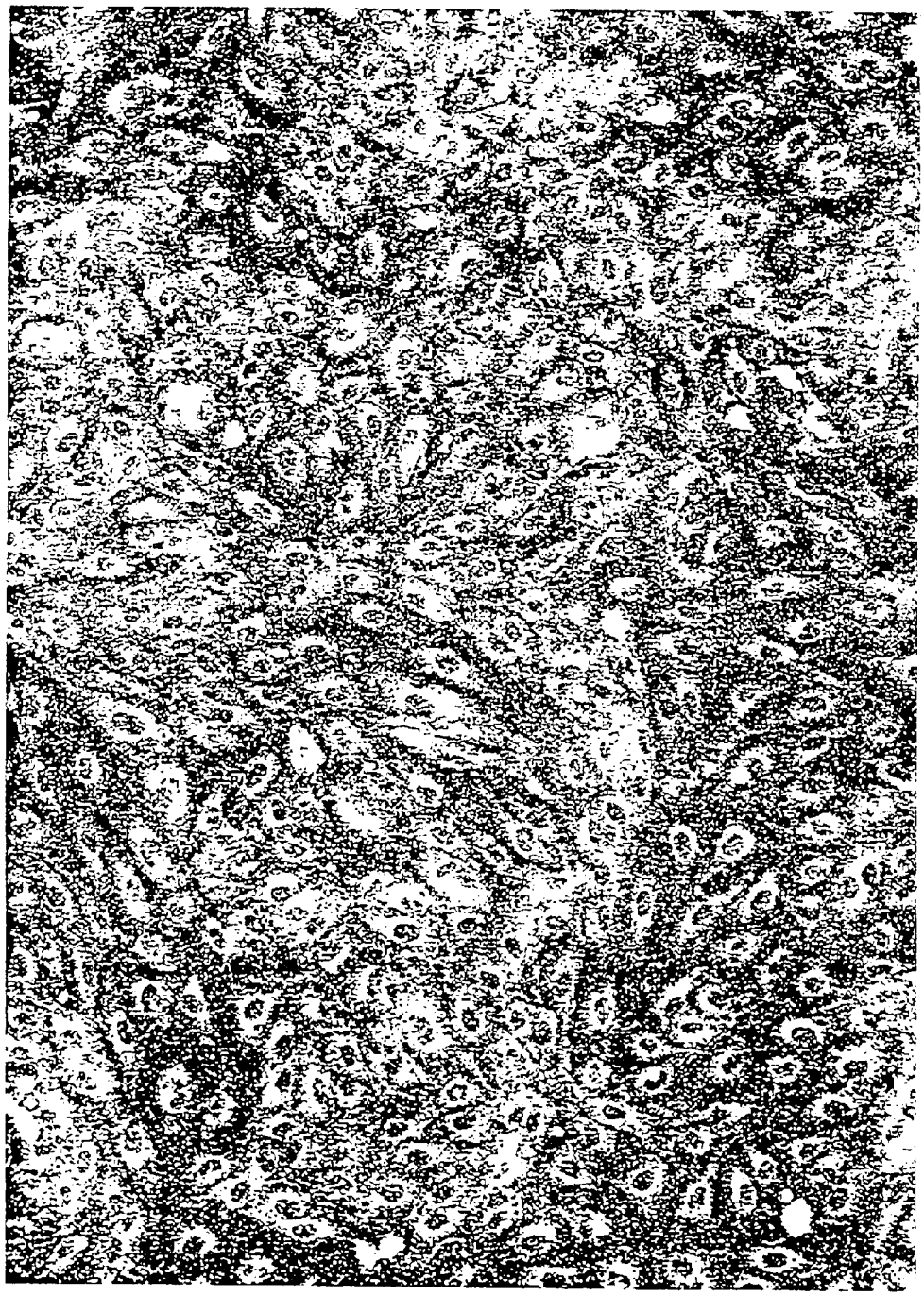

After seeding, cells on the BIOLASTIC disks showed good cell attachment to the surface within six hours. This was also seen in collagen-coated plates. On the day following seeding, the cells flattened on the surface of both the BIOLASTIC disks and the collagen-coated plates. They exhibited a characteristic polygonal and elongated endothelial cell morphology (FIG. 2A, FIG. 2B). A rapid increase in cell number was seen in the first two days following seeding of the BIOLASTIC disks and the collagen-coated plates (Table 1, FIG. 1). Between days 2 and 4 after seeding, endothelial cells continued to proliferate at similar rates on both the BIOLASTIC disks and the collagen-coated plates (Table 1, FIG. 1). After day 4, cell populations attained confluence and complete coverage of the BIOLASTIC disks and the collagen coated plates by a monolayer of cells (FIG. 3A, FIG. 3B). Beyond this time, no further increase in cell number was noted for either group.

TABLE 1

Growth of endothelial cells on collagen-coated plates versus BIOLASTIC disks.

| Days Following Seeding | Collagen Coated Plates n = 5 | BIOLASTIC Disks n = 5 |
| --- | --- | --- |
| 1 | 85 + 16 | 161 + 68 |
| 2 | 129 + 54 | 204 + 64 |
| 3 | 185 + 70 | 286 + 76 |
| 4 | 230 + 85 | 351 + 98 |

All values are reported as the mean±standard error from the mean.

Statistics

From the time of initial cell seeding to confluence of cell cultures, there was a greater number of cells on BIOLASTIC disks than the collagen-coated control plates. With five pairs of data at each time point, this difference attained statistical significance at the 1% level at all four time points ($p<0.01$) as performed by Student's two sample unpaired t-test.

When the combined data for the four days following seeding was taken together and analyzed using analysis of variance, the difference between the number of cells present on the BIOLASTIC disks compared to the collagen-coated plates was highly significant, $p<0.001$, with 7 degrees of freedom.

EXAMPLE 2

Experimental Details

A 50% solution of bovine albumin was made by dissolving 25 g bovine albumin in 50 ml deionized water at 37° C. to facilitate solubilization of the albumin. A 5% solution of glutaraldehyde was prepared from a stock glutaraldehyde solution of 25%. To create a thin coating on the lumenal surface of a small diameter vascular graft, 10 ml of glutaraldehyde pre-warmed to 37° C. was run, over a period of 30 seconds, down the lumen of a fresh pig carotid artery. This was achieved by holding one end of the artery by a cannula inserted and tied in place for support. Immediately following glutaraldehyde, 10 ml of albumin solution, pre-warmed to 37° C., was run down the lumen of the carotid artery over 30 seconds in a similar way to the glutaraldehyde solution. Immediately following the albumin, 10 ml of phosphate buffered saline at 37° C. was run through the lumen of the carotid artery over a 30 second period as a wash solution. Cross-sections of the carotid artery were then cut for examination of the surface coating integrity at various places along the length of the vessel. Similar coating treatments were carried out in fresh porcine and bovine ureters.

Results

The thickness of the glutaraldehyde/albumin coating was measured using a Nikon microscope fitted with a digital camera. Video images were measured using a computerized morphometric software routine to yield an average thickness of the coating. In general, coating thickness measurements yielded an average coating thickness of 28 microns (0.028 mm).

All documents cited above are hereby incorporated in their entirety by reference.

One skilled in the art will appreciate from a reading of this disclosure that various changes in form and detail can be made without departing from the true scope of the invention.

What is claimed is:

1. A method of inhibiting restenosis following vascular intervention comprising applying to a site of vascular injury resulting from said intervention a first composition comprising about 27–53% by weight of a water soluble globular protein and a second composition comprising about 5–15% by weight of a di- or polyaldehyde, wherein said di- or polyaldehyde is present in a weight ratio of one part by weight to every 20–60 parts by weight of said globular protein, and allowing said composition to cure so that a coating is produced at said site of vascular injury that inhibits restenosis.

2. The method according to claim 1 wherein said intervention is angioplasty.

3. The method according to claim 1 wherein said globular protein is albumin or hemoglobulin.

4. The method according to claim 3 wherein said globular protein is bovine albumin.

5. The method according to claim 1 wherein said aldehyde is glutaraldehyde.

6. The method according to claim 1 wherein said globular protein is bovine albumin and said aldehyde is glutaraldehyde.

7. The method according to claim 1 wherein said coating further comprising a therapeutic agent.

8. The method according to claim 7 wherein said therapeutic agent is selected from the group consisting of an anti-thrombotic agent, a thrombolytic agent, a vasodilating agent, a growth modulating factor and an antibiotic.

9. A method of providing structural support to a surface of a hollow or tubular organ comprising:

i) coating said surface with a first composition comprising about 27–53% by weight of a water soluble proteinaceous material and with a second composition comprising about 5–15% by weight of a di- or polyaldehyde, wherein said di- or polyaldehyde is present in said coating in a weight ratio of one part by weight to every 20–60 parts by weight of said proteinaceous material, and ii) allowing the product of step (i) to cure so that said structural support is provided.

10. The method according to claim 9 wherein said proteinaceous material a globular protein.

11. The method according to claim 9 wherein said proteinaceous material is albumin or hemoglobin.

12. The method according to claim 9 wherein said aldehyde is glutaraldehyde.

13. The method according to claim 9 wherein said proteinaceous material is bovine albumin and said aldehyde is glutaraldehyde.

14. The method according to claim 9 wherein said surface is selected from the group consisting of the surface of a vein, artery ureter, urethrae, bronchi, biliary duct, pancreatic duct, gut, eye, nasal passage, sinus, capsular joint, esophagus, lymphatic system, trachea, spermatic tube and fallopian tube.

15. The method according to claim 9 wherein said surface is coated with said second composition and then with said first composition.

16. A method of occluding a tissue lumen comprising:

i) introducing into said lumen a first composition comprising about 27–53% by weight of a water soluble proteinaceous material and a second composition comprising about 5–15% by weight of a di- or polyaldehyde, wherein said di- or polyaldehyde is present in a weight ratio of one part by weight to every 20–60 parts by weight of said proteinaceous material, and ii) allowing the product of step (i) to cure so that said lumen is occluded.

17. The method according to claim 16 wherein said proteinaceous material a globular protein.

18. The method according to claim 16 wherein said proteinaceous material is albumin or hemoglobin.

19. The method according to claim 16 wherein said aldehyde is glutaraldehyde.

20. The method according to claim 16 wherein said proteinaceous material is bovine albumin and said aldehyde is glutaraldehyde.

21. The method according to claim 16 wherein said second composition is introduced into said lumen prior to said first composition.

22. A composition comprising a support and cells adhered thereto, wherein said support is produced by a method comprising:

i) contacting a first composition comprising about 27–53% by weight of a water soluble proteinaceous material and with a second composition comprising about 5–15% by weight of a di- or polyaldehyde, wherein said di- or polyaldehyde is present in a weight ratio of one part by weight to every 20–60 parts by weight of said proteinaceous material, and ii) allowing the product of step (i) to cure so that said support is thereby produced.

23. The method according to claim 22 wherein said proteinaceous material a globular protein.

24. The method according to claim 22 wherein said proteinaceous material is albumin or hemoglobin.

25. The method according to claim 22 wherein said aldehyde is glutaraldehyde.

26. The method according to claim 22 wherein said proteinaceous material is bovine albumin and said aldehyde is glutaraldehyde.

27. A method of providing structural support to a surface of a hollow or tubular organ comprising:

i) applying to said surface a coating comprising a water soluble proteinaceous material and a di- or polyaldehyde, wherein said di- or polyaldehyde is present in said coating in a weight ratio of one part by weight to every 20–60 parts by weight of said proteinaceous material, and ii) allowing the coating of step (i) to cure so that said structural support is provided.

28. The method according to claim 27 wherein said proteinaceous material a globular protein.

29. The method according to claim 27 wherein said proteinaceous material is albumin or hemoglobin.

30. The method according to claim 27 wherein said aldehyde is glutaraldehyde.

* * * * *